United States Patent [19]

Poncy

[11] Patent Number: 4,961,730
[45] Date of Patent: Oct. 9, 1990

[54] HYPODERMIC SYRINGE WITH SLIDING CAP

[76] Inventor: George W. Poncy, 3725 Investment La., Riviera Beach, Fla. 33404

[21] Appl. No.: 414,005

[22] Filed: Sep. 29, 1989

[51] Int. Cl.$^5$ ............................................... A61M 5/32
[52] U.S. Cl. ..................................... 604/198; 604/263
[58] Field of Search ............... 604/198, 192, 263, 187

[56] References Cited

U.S. PATENT DOCUMENTS

| | | | |
|---|---|---|---|
| 4,816,022 | 3/1989 | Poncy | 604/198 |
| 4,842,587 | 6/1989 | Poncy | 604/198 |

*Primary Examiner*—John D. Yasko
*Attorney, Agent, or Firm*—Lane, Aitken & McCann

[57] ABSTRACT

A needle and cap assembly for attaching to a hypodermic syringe body includes a needle mounting structure, a needle, and a cap slideably mounted on the needle mounting structure. The needle mounting structure includes a hub, arcuate bands making a sliding fit with an interior surface of the cap, and spokes connecting the bands to the hub. Each band has a profiled tail end including an indent, which cooperates with an axial guide rail on the interior surface of the cap, to allow the cap to be selectively rotated between a first position, in which the cap is retained in an extended position covering the needle, and a second position, in which the cap may be moved in guided axial motion to a retracted position exposing the needle.

10 Claims, 2 Drawing Sheets

U.S. Patent  Oct. 9, 1990  Sheet 1 of 2  4,961,730
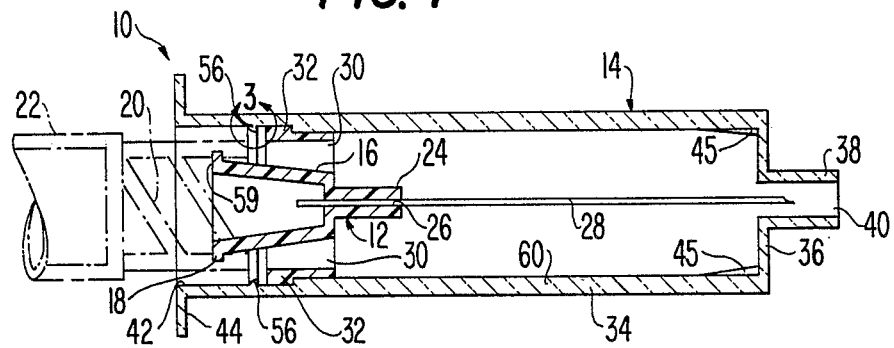
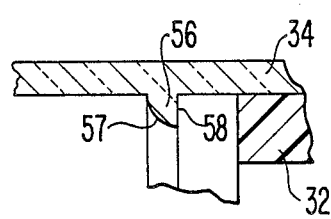
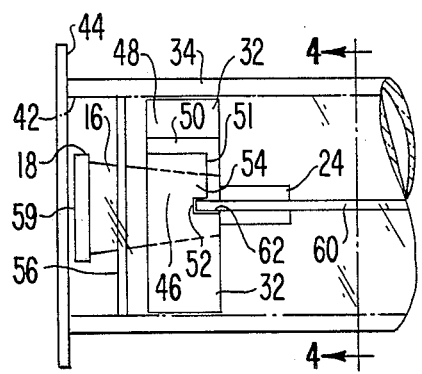
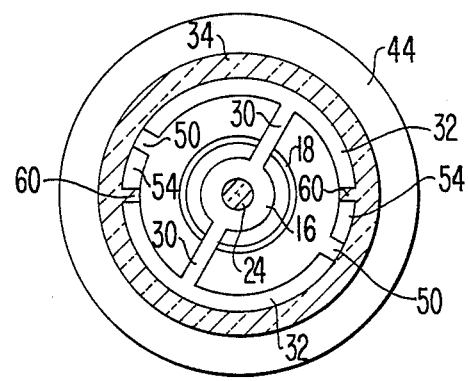

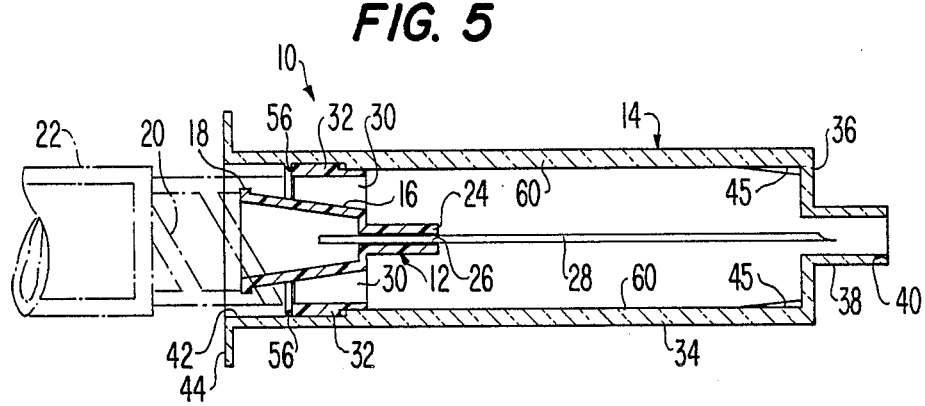
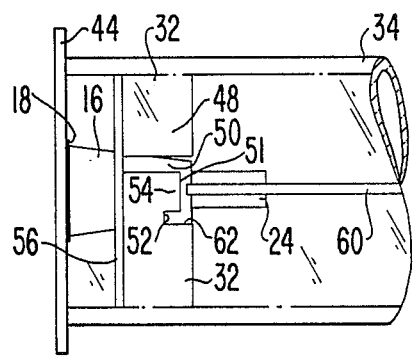
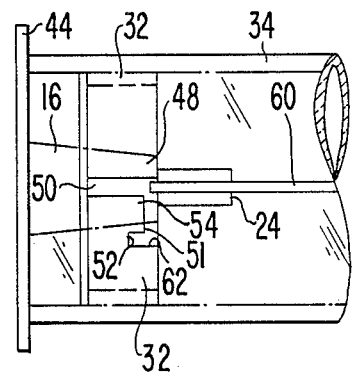
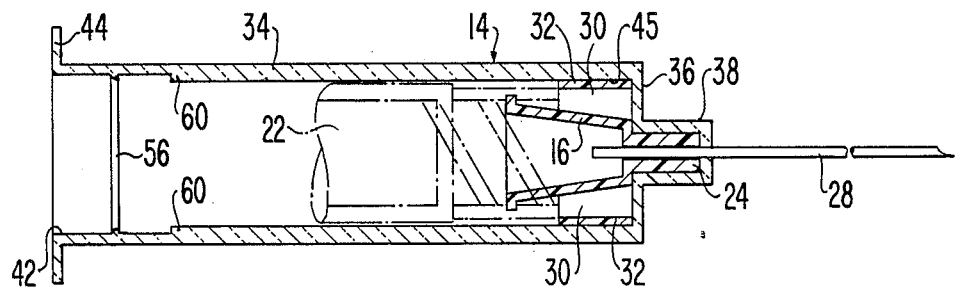

HYPODERMIC SYRINGE WITH SLIDING CAP

BACKGROUND OF THE INVENTION

This invention relates to hypodermic syringes for withdrawing blood or infusing a patient with serums and the like and, more particularly, to a hypodermic syringe designed to prevent accidental pricking of the fingers or hands of the person using the syringe.

With conventional hypodermic syringes, the administration of an injection or blood withdrawal involves the removal of a protective cap covering the needle of the syringe and, after the withdrawal of the needle from the body of a patient, the replacement of the cap over the needle before the needle is discarded. The procedures just described can easily lead to the accidental pricking of a hand or finger of the administrant, the injection of harmful viruses and bacteria under the skin, and the resultant infection of the administrant. In view of the increasing occurrence of fatal diseases such as Acquired Immune Deficiency Syndrome (AIDS), it is absolutely essential that accidental needle pricks be avoided.

Accidental pricking occurs most often during the removal and replacing of the needle cap. It is at these moments that the hand of the administrant is nearest to the sharp needle point. More specifically, the most common accidental pricking occurs because the cap is firmly held in place over the needle by friction between the cap and a hub in which the needle is mounted. A large frictional force is intentionally provided, such as by the engagement of ribs formed on an external surface of the needle hub and on an internal surface of the cap, so that the cap does not inadvertently become dislodged from the needle and thereby cause the previously sterile needle to become contaminated. In order to overcome the frictional resistance, the administrant must firmly grasp the cap and pull. The release of the cap from the needle hub occurs suddenly, so that there is a tendency for the hand to whip back towards the exposed needle, causing an accidental prick to occur. Accidental pricking also occurs when the cap is being replaced over the needle, since the opening in the cap into which the needle must be inserted is quite small. As a result, a slight misjudgment or unsteadiness causes the needle, instead of entering the small cap opening, to miss the opening and prick the finger of the administrant, which, by virtue of holding the cap, must of necessity be near the cap opening. In fact, such accidental pricking occurs even though caps of excessive length are used to cover even a short needle in an effort to increase the distance between the needle and the administrant's hand. For example, a cap used to cover a 1½ inch long needle may be as much as 2 inches long.

U.S. Pat. No. 4,842,587, issued on June 27, 1989 to the present inventor, describes a hypodermic needle assembly which overcomes the problems of accidental pricking in the removal and replacement of the needle caps. In the assembly of the application, a cap is incorporated as an integral part of the hypodermic unit, so that the cap requires no removal or replacement. The cap is slidably mounted on formations projecting from a hub in which the needle is mounted. The projecting formations include flaps projecting radially from the hub and resilient bands extending arcuately in one direction from the flaps to contact and guide the cap, maintaining the longitudinal axis of the cap in substantial alignment with the longitudinal axis of a syringe needle. As a result, any danger of the needle piercing a sidewall of the cap, especially during the sliding of the cap, is avoided. The cap has a diameter larger than the diameter of the syringe and a proximal end which is open to permit the cap to move down over the syringe and slide on the arcuate resilient bands. An opposite end of the cap is closed in the sense that there is no opening large enough for a finger to enter and come into contact with the needle. There is, however, an opening large enough for the needle to pass through to reach an exposed position in which an injection or withdrawal can be administered.

In one embodiment disclosed in the aforesaid patent, the cap is retained in the extended position by the engagement of the resilient bands with an annular interference bead on the inner surface of the cap, spaced from the proximal end of the cap, and the separation of the cap from the needle and the needle hub is prevented by the engagement of the resilient bands with an annular stop bead on the inner surface of the cap adjacent the proximal end. In addition, elongate axial ribs on the interior surface of the cap are received in gaps provided between the flaps and adjacent free ends of the arcuate resilient bands. Rotation of the cap causes the elongate ribs to push the bands and, thereby, rotate the needle hub to screw it onto the barrel of the syringe.

U.S. Pat. No. 4,816,022, issued on Mar. 28, 1989 to the present inventor, discloses a hypodermic syringe with a sliding cap which is an improvement in that disclosed in the aforesaid embodiment of U.S. Pat. No. 4,842,587 in that it reduces the chances of the cap being accidentally slid to a position to expose the needle and also facilitates molding the needle hub to provide a more uniform frictional force between the resilient bands and the interior wall of the cap. In accordance with the improvement, the annular stop bead on the inner surface of the cap, instead of being adjacent to the proximal end of the cap, is spaced inwardly from the proximal end so that when the cap is positioned on the needle hub with the resilient bands in engagement with the stop bead, the lower end of the needle hub will be approximately aligned with the lower end of the cap. In addition, in the improvement, instead of having a single resilient band extending from each flap in one direction a little less than 180 degrees, two resilient bands extending in both circumferential directions from each flap for a little less than 90 degrees wherein four resilient bands are provided instead of two and the resilient bands are considerably shorter. By reducing the length of the bands to a little less than 90 degrees, the frictional force with which the bands engage the cap is made more nearly uniform from unit to unit, and as a result, the amount of force required to slide the cap on the needle hub assembly is made more nearly uniform in different manufactured units.

In another embodiment disclosed in U.S. Pat. No. 4,842,587, the flaps include portions extending radially beyond the resilient bands, and the cap defines channels for receiving the flaps. The channels widen abruptly, at their ends adjacent to the syringe, to define slots into which the radially extending portions of the flaps can be twisted to lock the cap in its extended position.

SUMMARY OF THE INVENTION

By the present invention, a sliding cap assembly is provided for a hypodermic syringe wherein the cap slides on a needle hub having a profile such that rotation of the cap relative to the hub allows the cap to be either locked in an extended position covering the needle of the hypodermic syringe or slidable between the extended position and the retracted position, in which the needle is exposed.

More specifically, arcuate bands are connected to the needle hub by spokes. An end of each band extending circumferentially beyond the spokes defines a gap with an opposite end of an adjacent band and also defines a profile in which the band includes a lug having a smaller axial dimension than the rest of the band and an indent, between the lug and the rest of the band, which has a still smaller axial dimension. The profiled bands cooperate with foreshortened guide rails formed on the inner surface of the cap so that the cap can be moved between a first, locked position, in which ends of the foreshortened ribs are frictionally held in the indents to hold the cap in an extended position covering the needle, and a second, released position in which the foreshortened ribs are in alignment with the gaps between bands, so that the cap can be slid on the needle hub to a retracted position in which the needle is exposed. Movement of the hub from the locked position to the released position requires extension of the cap to a fully extended position and rotation of the cap relative to the hub and bands until the guide rails engage end surfaces of the adjacent bands.

The sliding cap according to the present invention eliminates the need for an interference bead in the cap between the hub and the closed end of the cap. Furthermore, movement of the cap from the locked position to a released position permitting retraction of the cap and exposure of the needle is resisted by a friction fit of the guide rails in the indents and requires initial movement extending and rotating the cap before movement in the opposite direction permitting retraction of the cap and exposure of the needle can be accomplished.

The inside diameter of the cap at the closed end is slightly smaller than the rest of the cap and slightly smaller than the diameter of the arcuate hub bands so that when the cap is fully retracted and the needle is fully exposed, the cap is firmly retained in the retracted position so as to prevent the cap from extending during use of the syringe. To re-cover the needle, the procedure is reversed so that the hub is securely held in the locked position within the cap. The syringe constitutes a trigger without which the assembly of the needle hub within the cap cannot be made to function to expose the needle.

BRIEF DESCRIPTION OF THE DRAWINGS

FIG. 1 is a cross-section of the sliding cap assembly according to the present invention in place on a syringe, with the cap in a locked position wherein the cap covers the needle;

FIG. 2 is a fragmentary top plan view of the cap assembly of FIG. 1;

FIG. 3 is an enlarged fragment of the cap assembly of FIG. 1, showing a stop bead;

FIG. 4 is a cross-section taken along the line 4—4 in FIG. 2;

FIG. 5 is a cross-section of the cap assembly according to FIG. 1 wherein the cap is in a fully extended transitional position between a locked position and a released position allowing axial movement of the cap and exposure of the needle;

FIG. 6 is a fragmentary top plan view of the cap assembly of FIG. 5;

FIG. 7 is a fragmentary top view of a cap assembly according to the present invention wherein the cap is fully extended in a released position allowing axial movement between the cap and the hub; and FIG. 8 is a cross-section of the cap assembly according to the present invention in which the cap is retracted and the needle is exposed.

DETAILED DESCRIPTION OF THE PREFERRED EMBODIMENT

As can be seen from FIG. 1, the cap assembly of the invention, which is designated generally by the reference numeral 10, comprises a needle portion 12, and a closure or cap portion 14 enclosing the needle portion 12. The needle portion 12 includes a hollow conical needle hub 16 with a rim 18 for connecting with the male threads 20 of a syringe body 22 in a Luer lock. A cylindrical post 24 on the needle hub 16 has a bore 26 for receiving a needle 28. Two spokes 30 project radially from the needle hub 16, and an arcuate resilient band 32 extends in each direction from the radially outer end of each spoke 30 to free ends spaced by a gap 50 from the opposite ends of the other band 32. Each spoke 30 has an axial dimension equal the largest axial dimension of the arcuate bands 32. Although just two spokes 30 are illustrated, additional spokes having axial dimensions the same as or smaller than the axial dimension of the spokes 30 can be employed to provide additional support for the arcuate bands 32.

The bands 32 are integral with the spokes 30 and have a radius at their free ends slightly greater than the radius of the internal surface of a generally cylindrical cap body 34 when the bands 32 are in their unflexed state, that is, before they are inserted in the cap body 34. The areas of intersection of the bands 32 and the spokes 30 act as spring-loaded hinges to bias the ends of the bands 32 against the cap body 34, whereby the cap body can reciprocate by sliding on the bands without substantial wobble, thereby maintaining the longitudinal axis of the cap body 34 substantially aligned with the longitudinal axis of the needle 28.

The cap body 34 has a shoulder 36, a hollow cylindrical cap extension 38, a reduced-diameter opening 40, and a large opening 42. In addition, the cap body 34 includes an exterior annular flange 44 at its proximal end. Formed integrally on an inner surface of the cap body 34 are a plurality of tapered thin ribs 45 projecting gradually from the inner surface toward the axis of the cap body 34 as they progress to the shoulder 36 from a point on the inner surface of the cap body spaced from the shoulder 36. Typically, four tapered ribs 45 are provided spaced circumferentially around the inner surface of the cap body 34 and beginning with a radial dimension of zero at ¼ inch from the shoulder 36 to a dimension of 0.002 inches at the shoulder 36. The tapered ribs 45 are also thin in the direction transverse to the radial direction. As the cap body 34 slides on the arcuate bands 32 to the fully retracted position of the cap body, the bands 32 engage the tapered ribs 45 with increasing interference. In this way, the cap portion 14 is firmly frictionally retained in a retracted position exposing the needle 28.

As can be seen from FIG. 2, in the preferred embodiment, the cap body 34 is made from transparent plastic so that the needle portion 12, including the needle hub 16 and the arcuate bands 32 can be seen through the cap body 34. A distinctively profiled tail end 46 of one arcuate band 32 and an opposite head end 48 of the other arcuate band 32 are spaced by a gap 50, so that the needle portion has two gaps 50 spaced 180 degrees apart. The tail end 46 has a smaller axial dimension than the rest of the arcuate band 32, extending from an arcuate edge of the band 32 proximal to the large opening 42 to an edge 51 parallel to but short of an arcuate edge distal to the large opening 42. An indent 52 parallel to the axis of the needle portion 12 is defined in the edge 51 of the tail end 46 adjacent to the juncture of the tail end with the portion of the arcuate band 32 having the largest axial dimension. Thus, the needle portion 12 has two indents 52 spaced 180 degrees apart. Each indent 52 has an even shorter axial dimension than the rest of the tail end 46, thereby defining a lug 54 between the indent and the gap 50.

As can best be seen from FIG. 3, an annular stop bead 56 is formed on the inner surface of the cap body 34 in a plane spaced slightly inward from the exterior annular flange 44. The annular stop bead 56 has the cross-section of a 90 degree sector of a circle with a curved surface 57 facing toward a proximal end of the cap body 34 and a flat surface 58 facing toward the distal end of the cap body. The flat surface 58 of the stop bead 56 is spaced from the end of the cap body 34 having the large opening 42 by a distance equal to the distance between the arcuate edge of the band 32 proximal to the large opening 42 and a bottom surface of the rim 18 of the conical needle hub 16 facing the syringe body 22 so that, when the needle portion 12 is inside the cap portion 14, with the bands 32 in engagement with the flat side of the stop bead 56, the bottom surface of the rim 18 of the needle hub 16 will be aligned approximately with the end of the cap body 34. During assembly of the needle portion 12 with the cap portion 14, as the arcuate bands 32 are forced past the stop bead 56, the curved surface 57 deflects the bands radially inward. When the arcuate bands 32 have popped past the stop bead 56, the flat surface 58 prevents the arcuate bands from passing back past the stop bead and, thereby, prevents the needle portion 12 from separating from the cap portion. The distance between the flat surface 58 of the stop bead 56 and the shoulder 36 of the cap body 34 is less than the distance between the surface of the arcuate bands 32 proximal to the stop bead 56 to tip of the needle 28, so that after the needle portion 12 has been assembled with the cap portion 14, a portion of the needle 28 always lies within the hollow cylindrical cap extension 38.

The distance between the flat surface 58 of the stop bead 56 and the open end of the cap body is at least as great as the distance between the arcuate edge of the arcuate bands 32 proximal to the large opening 42 and an end surface 59 of the needle portion 12 adjacent to said large opening 42. By this arrangement, the open end of the cap body 34 protects the needle portion 12 from accidental forward movement in the cap body exposing the needle 28. Even the large opening 42 is small enough that a thin object, such as a pencil or a small finger would be required to engage the needle portion 12 to move it forward in the cap body 34.

As can be seen from FIGS. 1, 2 and 4, a pair of foreshortened guide rails 60, integrally formed on an interior surface of the cap body 34, are spaced 180 degrees apart from one another so that they can selectively align with the gaps 50, in one position, and with the indents 52 in another position. The guide rails 60 extend axially from the shoulder 36 to a point spaced from the stop bead 56, the distance between the stop bead 56 and the ends of the guide rails 60 proximal to the stop bead being less than the axial dimension of the arcuate bands 32. Thus, the guide rails 60 must be aligned with spaces between a shoulder 62 on the tail end 46 of one arcuate band 32 and the head end 48 of the other arcuate band 32 so that there is sufficient axial distance for the arcuate bands 32 to pass completely beyond the stop bead 56. With the needle portion 12 and the cap portion 14 assembled and the ends of the guide rails 60 somewhere in the spaces between the shoulders 62 and the head ends 48, for example, in the position shown in FIGS. 5 and 6, when the needle portion 12 is rotated upward as viewed in FIG. 2 by turning the syringe body 22 to which the needle portion is connected, the needle portion cannot rotate beyond the engagement of the guide rail 60 with the shoulders 62. A small movement of the syringe body 22 and, thus, the needle portion 12 axially into the cap body 34 causes the insertion of the ends of the guide rails 60 into the indents 52. Each indent 52 has a width slightly smaller than the width of the guide rails 60 to cause the arcuate band 32 to be frictionally retained on the end of the guide rail. In this position, the needle 28 is covered by the cap and cannot extend to an exposed position. At least one of the needle portion 12 and the cap portion 14, and preferably both, are made of a resilient plastics material.

As can be appreciated from FIG. 7, when considered in connection with FIG. 2, in order to release the needle portion 12 from its frictionally held locked position, the cap portion 14 must be extended until the edge 51 of the lug 54 distal to the stop bead 56 is closer to the stop bead than the proximal end of the guide rail 60 is. The stop bead 56 prevents removal of the needle portion 12 from the cap portion 14 during this movement. Then the needle portion is rotated downward as viewed in FIGS. 2 and 7 until the guide rail 60 engages the head end 48 surface of the other arcuate band 32, which prevents further rotational movement. In this position, the gap 50 between the adjacent ends of the arcuate bands 32 is in alignment with the guide rail 60 and is wider than the guide rail so that the needle portion 12 can be moved toward the reduced-diameter opening 40 of the cap to expose the needle 28, as is shown in FIG. 8. The thin ribs 45 on the internal diameter of the cap body 34 adjacent to the shoulder 36 frictionally retain the cap body 34 in its retracted position while the syringe is in use.

When the use is complete, the cap body 34 is extended until the arcuate bands 32 contact the stop bead 56. Then the cap body is rotated until the shoulder 62 contacts the guide rail 60, and the cap body is moved in its retracting direction, locking the arcuate band 32 on the guide rail 60 in a position in which the cap covers the needle 28 and prevents exposure of the needle. When the guide rails 60 are positioned in the gaps 50 or in the indents 52, the needle portion 12 is prevented from any rotational movement relative to the cap body 34. In any other position, the needle portion 12 is capable of only limited rotational movement relative to the cap body 34. Thus, in any position of the needle portion 12 relative to the cap body, the syringe body 22 can be connected to the rim 18 on the hollow conical needle hub 16 of the needle portion 12 by holding the cap body 34 with one hand and the syringe body 22 with the other hand and rotating the syringe body relative to the cap body.

The foregoing description has been of the action of one guide rail 60 with the profiled tail end 46 of one arcuate band 32 adjacent another arcuate band. The same action takes place with respect to the other guide rail 60 and tail end 46 of the embodiment shown. It is understood that other numbers of guide rails 60 and arcuate bands 32, defining corresponding numbers of appropriately spaced gaps 50 and indents 52, can be used. Furthermore, it is contemplated that other modifications of the preferred embodiment described herein may be made without departing from the spirit and scope of the invention, which is defined in the appended claims.

I claim:

1. A needle and cap assembly for attaching to a hypodermic syringe body comprising a needle, means for mounting said needle, said needle mounting means having means for securing said needle mounting means on the syringe body, a cap slideably mounted on said needle mounting means between a first position in which said cap covers said needle and a second position in which said cap exposes said needle, said needle mounting means having bands making a sliding fit with an interior surface of said cap, and means for selectively locking said cap in said first position, a first structure on said bands and a second structure on an interior surface of said cap, said first structure and said second structure being selectively engageable with one another.

2. A needle and cap assembly as recited in claim 1, wherein said first structure comprises an indent in said bands and said second structure comprises a formation on said cap engageable with said indent.

3. A needle and cap assembly as recited in claim 1, further comprising means for preventing separation of said cap from said needle mounting means, said separation preventing means comprising a stop bead on an interior surface of said cap.

4. A needle and cap assembly as recited in claim 3, wherein the cap includes an open end having an opening large enough to allow insertion of the syringe body, and the stop bead is spaced from the open end of the cap body by a distance at least as great as the distance between an edge of the bands proximal to said open end and an end surface of said needle mounting means proximal to said open end of said cap, whereby said needle mounting means is flush with said open end of said cap.

5. A needle and cap assembly as recited in claim 2, wherein said formation on said cap is a guide rail extending axially on the interior surface of said cap.

6. A needle and cap assembly as recited in claim 5, wherein said bands are made of resilient material and said indent has a first width, said guide rail having a second width slightly greater than said first width, whereby said needle mounting means frictionally retains said cap in its first position.

7. A needle and cap assembly as recited in claim 3, wherein the bands have a first edge proximal to said stop bead and a second edge distal to said stop bead, and at least one of said bands has a tail end having a first edge lying in the same plane as said first edge of said bands and a second edge parallel to said first edge of said bands and lying closer to said first edge of said bands than said second edge of said bands does, whereby said tail end has a smaller axial dimension than said bands, said tail end having an end surface, and said indent being defined in said second edge of said tail end spaced from said end surface.

8. A needle and cap assembly as recited in claim 7, wherein the distance between said first and second surfaces of said bands is greater than the distance between said formation on said cap and said stop bead, whereby, when said first edge of said bands engages said stop bead, at least a portion of said formation lies between planes containing said second edge of said bands and said second edge of said tail end.

9. A needle and cap assembly as recited in claim 1, wherein each of said bands includes an indent, and said cap includes a formation engageable with each of said indents.

10. A needle and cap assembly as recited in claim 1, wherein said cap includes a cylindrical interior surface and a substantially closed end, and the needle and cap assembly further comprises a plurality of tapered ribs on said cylindrical interior surface adjacent to said substantially closed end.

* * * * *